United States Patent
Mc Hale et al.

(10) Patent No.: US 7,160,317 B2
(45) Date of Patent: Jan. 9, 2007

(54) MULTIPLE-WING BALLOON CATHETER TO REDUCE DAMAGE TO COATED EXPANDABLE MEDICAL IMPLANTS

(75) Inventors: Tom Mc Hale, Furbo (IE); Jan Weber, Tuam (IE); Timothy O'Connor, Claregalway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 543 days.

(21) Appl. No.: 10/035,218

(22) Filed: Jan. 4, 2002

(65) Prior Publication Data
US 2003/0130717 A1    Jul. 10, 2003

(51) Int. Cl.
*A61F 2/06* (2006.01)
(52) U.S. Cl. ..................... 623/1.11
(58) Field of Classification Search .......... 623/1.11, 623/1.1, 1.13, 1.23, 1.42; 606/191–192, 606/194, 195, 108; 604/96.01, 103.05, 103.06, 604/103.08, 103.14
See application file for complete search history.

(56) References Cited
U.S. PATENT DOCUMENTS

| | | | |
|---|---|---|---|
| 5,087,246 A | 2/1992 | Smith | 604/96 |
| 5,116,318 A * | 5/1992 | Hillstead | 604/103.14 |
| 5,147,302 A | 9/1992 | Euteneuer et al. | 604/103 |
| 5,209,799 A | 5/1993 | Vigil | 156/156 |
| 5,290,306 A * | 3/1994 | Trotta et al. | 606/194 |
| 5,342,307 A | 8/1994 | Euteneuer et al. | 604/103 |
| 5,350,361 A | 9/1994 | Tsukashima et al. | 604/96 |
| 5,352,236 A * | 10/1994 | Jung et al. | 606/194 |
| 5,456,666 A | 10/1995 | Campbell et al. | 604/96 |
| 5,690,670 A | 11/1997 | Davidson | |
| 5,718,684 A | 2/1998 | Gupta | 604/96 |
| 5,792,172 A | 8/1998 | Fischell et al. | 606/198 |
| 6,033,380 A | 3/2000 | Butaric et al. | 604/96 |
| 6,153,252 A * | 11/2000 | Hossainy et al. | 427/2.3 |
| 6,159,229 A | 12/2000 | Jendersee et al. | |
| 6,273,913 B1 * | 8/2001 | Wright et al. | 623/1.42 |
| 6,296,655 B1 | 10/2001 | Gaudoin et al. | |

* cited by examiner

*Primary Examiner*—(Jackie) Tan-Uyen T. Ho
(74) *Attorney, Agent, or Firm*—Kenyon & Kenyon LLP

(57) ABSTRACT

Method and system for reducing the damage to a coated medical implant during the expansion of the coated implant is provided. The method may include providing a coated medical implant, providing a balloon catheter having a multi-wing balloon, the multi-wing balloon having at least four expandable folds, and crimping the medical implant onto the multi-wing balloon. The system may include a coated medical implant and a multi-wing balloon catheter having at least four expandable wings, the expandable wings in contact with the coating of the medical implant.

9 Claims, 3 Drawing Sheets

US 7,160,317 B2

MULTIPLE-WING BALLOON CATHETER TO REDUCE DAMAGE TO COATED EXPANDABLE MEDICAL IMPLANTS

FIELD OF THE INVENTION

The present invention relates to methods and systems for deploying coated expandable medical implants. More particularly the present invention regards methods and systems that employ a multi-wing balloon catheter for deploying a coated medical implant at a target site.

BACKGROUND

Expandable medical implants are positioned and placed in the body during the completion of numerous contemporary medical procedures. These implants may include stents, vena-cava filters, and aneurism coils and may be used for innumerable purposes including reinforcing damaged vessels, replacing ruptured vessels, and delivering therapeutic to a target site in the body. This therapeutic may be delivered via coatings placed in, on, and around the implants as well as through various other means and methods.

When, for example, the therapeutic is delivered by a coated expandable implant, the coating can be damaged both during assembly and, afterwards, during the actual medical procedure. When an implant having a therapeutic coating is being assembled, the coating is routinely at risk of damage. For instance, during the crimping of balloon expandable stents onto their carrier balloon catheters, large compressive forces are exerted onto the coating of the stent in order to secure the stent to the balloon.

Even after a stent has been crimped onto a catheter, the coating is also at risk of being damaged during the delivery of the stent. For example, an expandable stent is often delivered by a balloon catheter that is expanded after the catheter reaches the target site. At a target site, when the stent is being deployed, as the balloon is expanded and both shear and torsional forces are placed on the coating by the expanding balloon. These forces can be counterproductive if too large because they can tear the coating away from and off of the stent. This tearing away can cause the therapeutic to be haphazardly adhered to the stent and, thus, reduce its effectiveness.

SUMMARY OF THE INVENTION

Method and system for reducing the damage to a coated medical implant during the expansion of the coated implant is provided. The method may include providing a coated medical implant, providing a balloon catheter having a multi-wing balloon, the multi-wing balloon having at least four expandable folds, and crimping the coated implant onto the multi-wing balloon. The system may include a coated medical implant and a multi-wing balloon catheter having at least four expandable wings, the expandable wings in contact with the coating of the medical implant.

DETAILED DESCRIPTION

Figure 1:
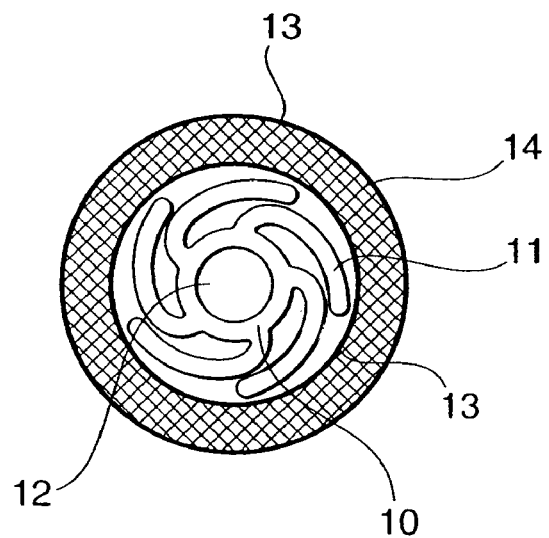
FIG. 1 is a cross-sectional view of a multi-wing balloon catheter carrying a coated implant in its pre-inflation state.

FIG. 1 is a cross-sectional view of the working end of a multi-wing balloon catheter in accord with one embodiment of the present invention. In FIG. 1 the multi-wing balloon 10, expandable folds 11, and internal lumen 12 of the catheter can all be seen. Also visible in FIG. 1 is a medical implant 14 with a coating 13, the implant 14 being placed around the multi-wing balloon 10.

The multi-wing balloon 10 in this embodiment may be used to deliver the implant 14 to numerous target sites both inside and outside of the human body. During its use a fluid may be forced down the internal lumen 12 to the multi-wing balloon 10 to inflate the multi-wing balloon 10. As more fluid is injected into the multi-wing balloon 10 the balloon 10 may begin to expand both near its core and out at its peripheral folds 11. As the multi-wing balloon 10 expands it may exert a force on the implant 14 via the expandable folds 11 that may be in contact with the coating 13 of the implant 14. Due to the orientation of the folds 11 in this embodiment the folds may place both compressive and shear forces on the coating 13 during expansion. The compressive force are mostly associated with the expansion of the implant while the shear forces largely stem from the skimming of the folds over the surface of the coating during expansion.

In this embodiment, five expandable folds extend from the main body of the balloon 10, however, in other embodiments, the number of folds can be increased or can be reduced to four. By increasing the number of folds 11 the magnitude of forces that each fold places on the coating will be reduced. Moreover, as the number of folds 11 increases the distance that each fold may have to travel may be reduced. Thus, increasing the number of folds can reduce the torsional forces placed on the implant during expansion. In addition, by increasing the number of folds the time needed to inflate the balloon may also be reduced due to the smaller internal volume of each of the folds.

In an alternative embodiment, the number of folds can be chosen to conform with or correlate with the number of cells in the implant. By regulating the number of folds in the balloon in relation to the number of cells in the implant, the amount of pinpoint loads placed on the implant by the balloon can be better controlled and regulated. For instance, if the implant were a stent that had five cells positioned next to each other to form a ring, the balloon may have five folds such that one fold may touch the interface between each of the cells and exert a force thereon during the expansion of the stent.

In the embodiment of FIG. 1, it is preferable that the coating 13 employed is resilient enough to resist the forces that will be placed upon it by the five expandable folds 11 during the expansion of the multi-wing balloon 10. Alternatively, if the coating 13 is unable to resist damage during expansion the number of expandable folds 11 can be increased (as described above) or the coating 13 may be modified or changed to better accommodate the inflating forces placed upon it. In each situation, when the resiliency of the coating is being evaluated, its properties at both ambient temperature and within the body should preferably be considered in order to avoid the situation where the coating remains intact if the balloon is inflated outside of the body but is removed if the balloon is inflated within the body.

Figure 2:
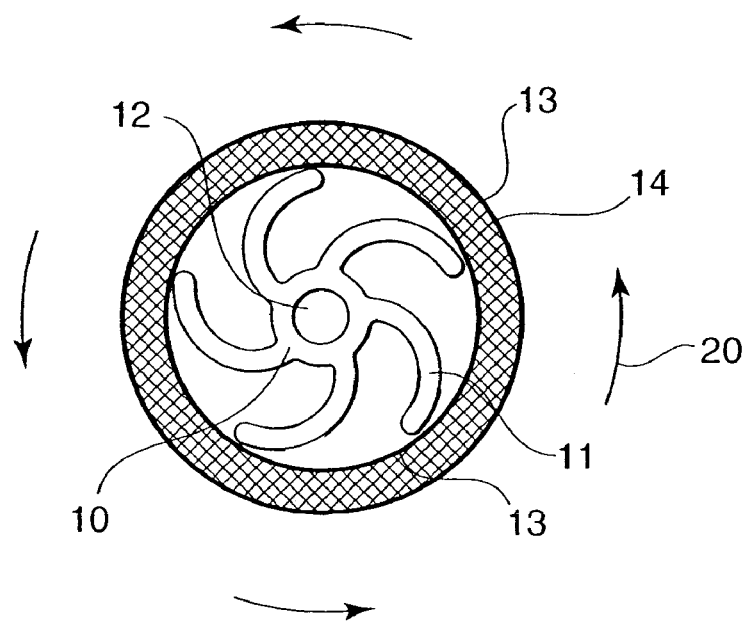
FIG. 2 is a cross-sectional view of the multi-wing balloon catheter of FIG. 1 after the balloon has begun to be inflated.

FIG. 2 is a cross-sectional view of the multi-wing balloon from FIG. 1 after the expandable folds 11 have begun to inflate and after they have begun to expand the implant 14. The arrows 20 indicate the path of rotation of the expandable folds as they inflate and push the implant 14 out. As can be seen, the folds 11 travel in a counter-clockwise direction in this embodiment. Alternatively, in a different embodiment, they could travel in a clockwise direction.

Also visible in FIG. 2 is the coating 13. As can be seen the coating 13 has not been substantially removed by the expansive forces of the folds although some slight repositioning and damage to the coating may have occurred.

Figure 3:
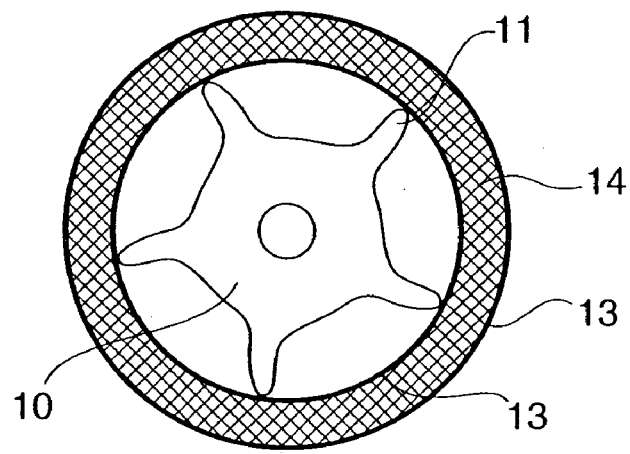
FIG. 3 is a cross-sectional view of the multi-wing balloon catheter of FIG. 1 wherein the balloon is in a semi-inflated condition.

FIG. 3 is a cross-section of the multi-wing balloon 10 after it has been partially inflated. In FIG. 3 the main portion of the balloon has grown larger and the folds 11 are no longer rotating within the implant 14 as in the earlier figures but have, instead, reached their fully extended position.

An advantage of the multiple folds 11 in this embodiment is the multiple contact points that they present during this stage of the expansion. By having five contact points with the coating 13, the coating 13 is less likely to be damaged during this phase of the expansion. Moreover, by increasing the number of folds, the unwanted expansion forces, associated with the nonuniform expansion of the implant along its longitudinal axis may be reduced. For instance, by increasing the number of folds, the angle by which the folds have to unfold during expansion is reduced, thereby further decreasing the forces that are placed on the implant during expansion. Likewise, by increasing the number of folds the risk of the balloon twisting and exerting torsional forces on the implant during expansion of the balloon is also reduced.

Figure 4:
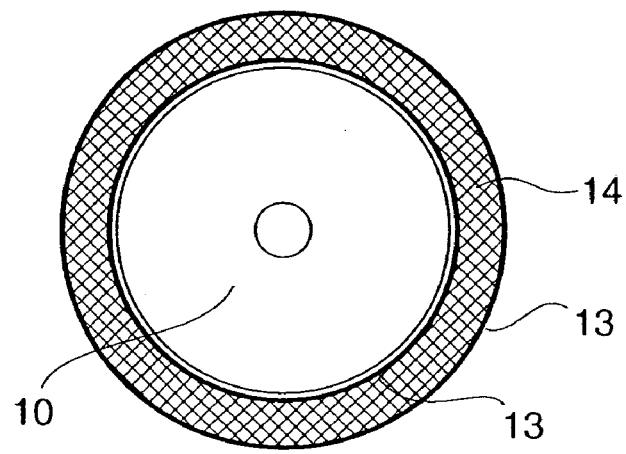
FIG. 4 is a cross-sectional view of the multi-wing balloon catheter of FIG. 1 in a fully inflated condition.

FIG. 4 is a cross-section of the multi-wing balloon from the earlier figures after it has been fully expanded. As is visible in FIG. 4 the coating 13 has remained substantially intact and both the balloon 10 and the implant 14 are larger than they were when the inflation process began. When being used in a medical procedure, after the implant has been enlarged to its desired size the balloon may then be deflated and removed from the implant, thereby leaving the implant at the target site.

The implant 14 may be any one of the numerous medical implants deployed at a target site by a balloon catheter including a stent. The coating 13 may also be one of various available coatings known to one of skill in the art used to coat these implants including a therapeutic agent, a biocompatible polymer, and a combination of both. In addition, the coating may be used to not only carry or transport therapeutic but also to facilitate the acceptance of the implant at the target site and to facilitate the rehabilitation of the target site.

Figure 5:
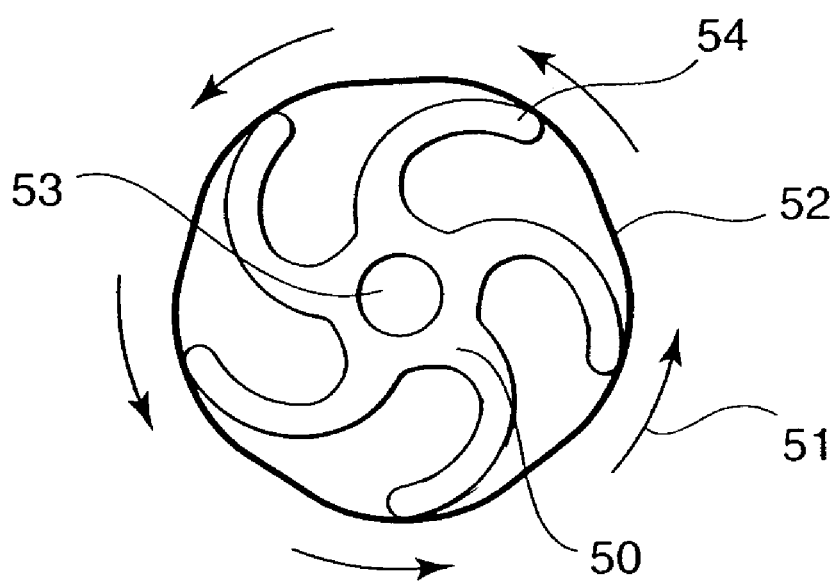
FIG. 5 is a cross-sectional view of a multi-wing catheter employing an expandable deformable membrane in accord with an alternative embodiment of the present invention.

FIG. 5 is an alternative embodiment of the present invention. In the embodiment of FIG. 5 the balloon 50 is surrounded by an elastic membrane 52. This membrane 52 may further reduce the destructive forces that can be placed on the coating 13 of a medical implant during its expansion. It is on top of this membrane 52 that a coated medical implant may be placed. This membrane 52 may be coated both on its inside and its outside in order to reduce the forces that may be generated between the membrane and the balloon and between the membrane and the implant.

FIG. 5 also shows the lumen 53, which may be used to inflate and deflate the balloon, located within the balloon 50 as well as arrows 51, which indicate the direction the folds 54 will rotate during the expansion of the balloon 50. The elastic membrane 52 may be made from latex as well as from other elastic materials. It is preferable that the membrane 52 be easily expandable as not to add a significant load to the balloon 50 during expansion. It is also preferable that the membrane be compatible with the coating so that it does not react or otherwise spoil the coating that may come in contact with it.

In addition to using an elastic membrane or in place of it the balloon may also be treated to reduce the friction between it and the implant that it will deliver. This treatment may include coating the balloon, heating the balloon to reduce its surface profile and polishing the balloon, also to reduce its surface profile.

The coatings employed may contain a therapeutic such as, for example: pharmaceutically active compounds, proteins, cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an antisense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

These therapeutic agents can be used, for example, in any application for treating, preventing, or otherwise affecting the course of a disease or tissue or organ dysfunction. For example, the embodiments of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

The coatings employed may also contain or be solely composed of various suitable polymers either alone or in combination with the above therapeutics. Suitable biocompatible polymers for use in the present invention can be hydrophilic or hydrophobic, and can include, but are not limited to, polycarboxylic acids, cellulosic polymers, including cellulose acetate and cellulose nitrate, gelatin, polyvinylpyrrolidone, cross-linked polyvinylpyrrolidone, hydrogels, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, ethylene vinylacetate, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

While various embodiments of the present invention have been disclosed herein other embodiments are also plausible without straying from the spirit and scope of the present invention.

What is claimed is:

1. A method of assembling a coated medical implant delivery system, the method comprising:
   providing an internally coated medical implant having an inner surface and an outer surface, the inner surface of the implant at least partially coated with a coating;
   providing a balloon catheter having a multi-wing balloon, the multi-wing balloon having a plurality of expandable folds;
   providing an elastic membrane sized to surround the expandable folds of the multi-wing balloon, the elastic membrane having a coating on an inside surface and on an outside surface;
   positioning the elastic membrane around the expandable folds of the multi-wing balloon; and
   positioning the medical implant around the elastic membrane after the elastic membrane has been positioned around the multi-wing balloon.

2. The method of claim 1 further comprising:
   crimping the coated medical implant around the elastic membrane and onto the multi-wing balloon.

3. The method of claim 1 further comprising:
   treating a surface of the folds of the multi-wing balloon to reduce friction.

4. The method of claim 3 wherein treating a surface of the folds of the multi-wing balloon to reduce friction includes polishing the balloon.

5. The method of claim 3 wherein treating a surface of the folds of the multi-wing balloon to reduce friction includes heating the balloon.

6. The method of claim 3 wherein the treatment includes coating the elastic membrane and wherein the implant is a stent.

7. The method of claim 1 wherein the multi-wing balloon expands in a sweeping spiral fashion.

8. The method of claim 1 wherein the elastic membrane comprises a latex.

9. The method of claim 1 wherein the coating of the medical implant includes a bio-compatible polymer and a therapeutic agent.

* * * * *